United States Patent [19]

Gullberg

[11] Patent Number: 4,984,159
[45] Date of Patent: Jan. 8, 1991

[54] METHOD AND APPARATUS FOR ESTIMATING ELLIPTICAL BODY CONTOURS IN FAN BEAM COMPUTED TOMOGRAPHIC SYSTEMS

[75] Inventor: Grant T. Gullberg, Salt Lake City, Utah

[73] Assignee: General Electric Company, Milwaukee, Wis.

[21] Appl. No.: 230,064

[22] Filed: Aug. 9, 1988

[51] Int. Cl.$^5$ .............................................. G06F 15/38
[52] U.S. Cl. ......................... 364/413.16; 364/413.22; 378/901
[58] Field of Search ...................... 364/413.16, 413.19, 364/413.22; 378/901

[56] References Cited

U.S. PATENT DOCUMENTS

| | | | |
|---|---|---|---|
| 4,044,240 | 8/1977 | Cox, Jr. et al. | 364/413.19 |
| 4,189,775 | 2/1980 | Inoye et al. | 364/413.19 |
| 4,293,912 | 10/1981 | Walters | 364/413.21 |
| 4,394,738 | 7/1983 | Wagner | 364/413.15 |
| 4,506,327 | 3/1985 | Jam | 564/413.19 |
| 4,672,651 | 6/1987 | Horiba et al. | 364/413.23 |
| 4,771,469 | 9/1988 | Wittenburg | 382/6 |

OTHER PUBLICATIONS

"Boundary Determination Methods For Attenuation Correction In Single Photon Emission Computed Tomography", Gullberg et al, *Emission Computed Tomography*, 1983.

Primary Examiner—Michael R. Fleming
Assistant Examiner—Gail O. Hayes
Attorney, Agent, or Firm—Leydig, Voit & Mayer

[57] ABSTRACT

A method and means is presented to estimate the contour of a body to compensate for attenuation in the production of a reconstructed image in fan beam computed tomographic systems having a detector system for taking a plurality of projections of a scanned body at a plurality of angles. The method and means defines a set of variable parameters representing an arbitrary ellipse and projects the arbitrary ellipse into fan beam projection space to determine the expected edges of the arbitrary ellipse at each angle in terms of the variable parameters. A series of fan beam projections is taken having sufficient information for reconstructing a cross-sectional image of the scanned body, and the fan beam coordinates of the apparent body edges in each of the projections are determined. The expected edges of the projected ellipse are fitted to the determined apparent body edge coordinates for each projection by iteratively optimizing all of the variable parameters of the arbitrary ellipse to determine a final set of parameters which defines an elliptical contour which best fits the scanned body. A cross sectional image of the body using the plurality of projections is then reconstructed and compensated by assigning attenuation values to the portion of the reconstructed image encompassed by the elliptical contour.

18 Claims, 4 Drawing Sheets

METHOD AND APPARATUS FOR ESTIMATING ELLIPTICAL BODY CONTOURS IN FAN BEAM COMPUTED TOMOGRAPHIC SYSTEMS

FIELD OF THE INVENTION

This invention relates to computed tomography, and more particularly to a method and means for defining the body contour and compensating for attenuation within the defined body contour in fan beam computed tomography reconstruction techniques.

BACKGROUND OF THE INVENTION

Computed tomography includes the principal fields of transmission computed tomography and emission computed tomography. Additionally, there are at least two distinct geometric systems in either transmission or emission computed tomography. The first is parallel beam geometry in which the source/detector relationship is such that all rays within any particular view are parallel to each other. The second is fan beam geometry in which the source/detector relationship is such that all rays within any view converge to a point. In one form of transmission computed tomography (TCT), an X-ray source and a multi-channel detector are fixed with respect to each other and mounted for rotation on a gantry on opposite sides of a patient aperture. During the course of a scan, a number of projections are taken which are later convolved and back projected to produce a pixelized image representing the linear attenuation coefficients of the slice of the body through which the radiation had passed.

In emission computed tomography (ECT), gamma emitting substances are ingested or injected into the body, following which the body is scanned to detect the concentration and distribution of the radioactive sources by taking projections at a plurality of angles around the body and reconstructing an image from these projections. An example of fan beam emission computed tomography is the rotating gamma camera used with a converging collimator. The collimator is intended to converge at a focal point a fixed distance from the gamma camera.

One of the factors accounted for in true fan beam reconstruction procedures is the diverging nature of the fan beam itself. The normal form of the Radon inversion relationship, on which many reconstruction techniques depend, assumes parallel beam geometry. When fan beam projections are reconstructed, the relationship between the parallel rays and the diverging rays is typically accounted for in or just prior to the convolution operation as well as in the back projection operation which must map the data according to the geometry of the system.

The problem of attenuation is one of the major complicating factors in image reconstruction with emission computed tomography. Among the problems that occur in ECT as a result of attenuation are "hot rim" artifacts and inaccurate data related to perceived asymmetrical organ uptake of injected radionuclides. Attenuation also reduces lesion contrast, and thus the detectability of interior lesions, and in addition, can cause volume deformation which makes it difficult to evaluate lesion size. Therefore, one of the difficulties involved in emission tomographic reconstruction procedures is to determine whether a count reduction is due to reduced perfusion or the ingested gamma emitting substances being attenuated within the body.

The first step in applying most attenuation correction procedures is the determination of the body contour or boundary. Once the boundary is determined, many procedures treat the entire body as having a constant attenuation coefficient. One approach to determining the body contour for reconstruction procedures is to fit the body contour to an ellipse, which is suitable for most cases. This may not be appropriate for all body contours, in which case the boundary may have to be defined by a more general convex boundary or, in a rare and most difficult case, a non-convex boundary.

As described above, most methods currently used obtain the body contour and assume a constant attenuation within the boundary. This is the method described in a paper co-authored by the instant inventor: Gullberg, Malko and Eisner, "Boundary Determination Methods For Attenuation Correction In Single Photon Emission Computed Tomography," *Emission Computed Tomography, Society of Nuclear Medicine*, pp. 33–53, 1983. In the above paper, a method for determining elliptical parameters which best estimate the body contour is presented but is limited to the field of parallel beam emission computed tomography.

While the method presented in the above paper is useful in the parallel beam geometry case, the estimating technique which is developed applies only to the parallel beam case, and cannot be used for the more general fan beam geometry. It is recognized, however, that in emission CT, fan beam collimators improve sensitivity and resolution over systems using parallel beam collimators. Without a method for determining elliptical parameters that best estimate the body contour when using fan beam collimators, practitioners have been faced with a number of alternatives, all of which have significant disadvantages.

A number of methods for determining the body contour have required multiple scans and are summarized below. A more detailed description may be found in the above mentioned Gullberg et al. paper entitled "Boundary Determination Method For Attenuation Correction In Single Photon Emission Computed Tomography." In these multiple scan techniques, preliminary scans obtain data relating only to the body outline. Further scans, however, are then required for the actual CT reconstructions.

One multiple scan method is the "point source" method. The point source method requires two projections in addition to the projections for the patient study. When the patient is lying supine on the imaging table, either a frontal or anterior view can measure the major axis of the ellipse, and a lateral view can measure the minor axis. For the major axis, a point source is positioned at an appropriate right and left lateral position. The distance between each centroid gives the length of the major axis. Adding together the projection coordinate for each centroid and dividing by two gives the location of one of the coordinates for the center of the ellipse. Likewise placing point sources on the patient anterior and posterior, a lateral view gives the length of the minor axis for the ellipse and the other coordinate for the center of the ellipse.

A second example of multiple scan techniques used to define the body contour when using fan beam reconstruction procedures is the use of an external ring of a gamma emitting source taped to the body. One data set is taken with the external ring source and one data set is taken without. Care must be taken to not move the patient between the two separate studies as the source is manipulated around the patient. The reconstruction of the projections with the ring source gives the body outline bounded by the ring of activity and the attenuation coefficient within the boundary is assumed to be constant.

A method presented in "Boundary Determination Methods For Attenuation Correction In Single Photon Emission Computed Tomography," discussed above, presents an alternative to these multiple scan techniques, but only for parallel beam systems. Specifically, on pages 43–46 of the article, the authors define a set of arbitrary elliptical parameters and present a method for determining the values for the parameters to define an ellipse which most closely represents the body contour. As previously mentioned, the article and method apply only to a parallel beam geometric system. Because of the parallel beam geometry, the method produces two chi-square functions to be optimized to yield the optimal values for the parameters of the ellipse. As noted on page 46, and as a direct consequence of the parallel beam geometry, one of the chi-square functions is simply a linear estimation problem that immediately determines the coordinates for the center of the ellipse. Therefore, two of the five required parameters are immediately apparent, while an iterative procedure is suggested to obtain the other three values.

Because of the diverging nature of the fan beam geometry, the above disclosed procedure cannot be applied to systems employing fan beam geometry. Consequently, in fan beam systems, the practitioner has been left to the multiple scan techniques discussed above. Conceptually, it would be possible to "rebin" the fan beam data into parallel beam data sets and proceed with the parallel beam method described, but as a practical matter that is not believed to have been accomplished because rebinning is inaccurate and introduces significant computational complications.

SUMMARY OF THE INVENTION

In view of the foregoing, it is a general aim of the present invention to define, from the projection data, the body contour in systems using fan beam reconstruction procedures for emission computed tomography.

More particularly, it is an object of the present invention to define, from the fan beam projection sets, an ellipse which most closely approximates the body contour when using fan beam geometric systems.

In greater detail, it is an object to fit body boundary projection data to an ellipse which most closely approximates the actual body contour in systems that use fan beam collimators.

A further object is to provide a procedure for estimating the body contour using only a single scan in systems using fan beam geometry.

The above objects are accomplished in accordance with the present invention in fan beam computed tomographic systems which have a detector system for taking a plurality of projections of a scanned body at a plurality of angles using the projection without the need for multiple scan techniques. A method and means is provided for estimating the body contour of the body to compensate for attenuation in the production of a reconstructed image. A set of variable parameters representing an arbitrary ellipse is defined and the expected edges of the arbitrary ellipse in fan beam projection space are determined at each angle in terms of the variable parameters. A plurality of fan beam projections of a body being scanned are taken at a plurality of angles and the fan beam coordinates of the apparent body edges in each of the projections are also determined. Thereafter, the expected edges of the projected ellipse are fitted to the determined apparent body edge coordinates for each projection by iteratively optimizing a function relating all of the variable parameters of the arbitrary ellipse to determine a final set of parameters which defines an elliptical contour which best fits the scanned body. Once the body contour is estimated, a cross sectional image of the body is reconstructed from the plurality of projections. The image, however, is compensated for attenuation by assigning attenuation values to the portion of the image encompassed by the estimated elliptical body contour.

Other objects and advantages will become apparent from the following detailed description when taken in conjunction with the drawings, in which.

While the invention will be described in connection with certain preferred embodiments, there is no intent to limit it to those embodiments. On the contrary, the intent is to cover all alternatives, modifications and equivalents included within the spirit and scope of the invention as defined by the appended claims.

DETAILED DESCRIPTION OF THE PREFERRED EMBODIMENT

Figures 1, 2:
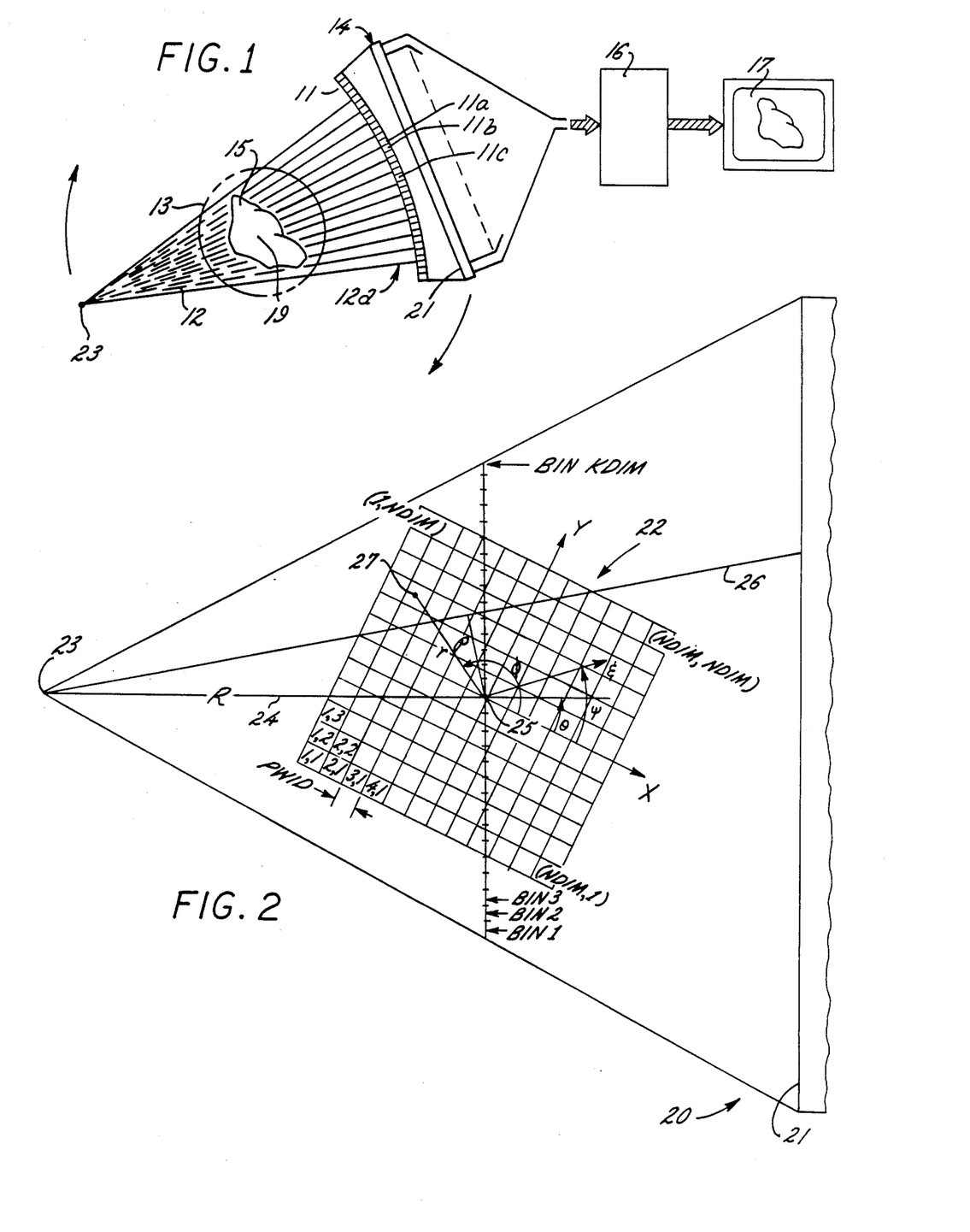
FIG. 1 is a diagram schematically illustrating a fan beam emission computed tomographic system.
FIG. 2 is a diagram illustrating a fan beam emission CT geometry and shows the relationship between bins in projection space and pixels in image space and defines the image space, parallel beam geometry and fan beam geometry coordinate systems.

Turning now to the drawings, FIG. 1 schematically illustrates the major elements of an emission fan beam CT scanning system. A body to be examined, such as a patient 15, is positioned within the patient aperture 13. Radionuclides within the body 15 emit radiation which is sensed by a rotating detector 14, usually in the form of a rotating gamma camera. Usually, the detector face is a flat crystal as illustrated at 21. Interposed between the gamma camera and the patient aperture is a converging collimator 11 which focuses the detector 14 to a focal spot 23 at the opposite side of the patient aperture and divides the fan into a plurality of beams 12, 12a. As a result, each collimator cell 11a, 11b, 11c, etc. produces an electrical signal on the detector which is dependent on the radiation energy received from each photon entering the cell. A set of such readings is called a projection, and a series or set of projections are taken as the source and detector rotate about the body.

The readings making up each projection are digitized and fed to a reconstruction computer 16 which can use one of a number of available procedures to produce the image of the cross section sensed by the fan beam. The image can be displayed on a monitor 17, or alternatively, can be used to create a film for further study by a diagnostician. It will be appreciated that in the illustrated example, the collimator 11 and detector 14 are mounted in a gantry for rotation about a point 19 within the patient aperture.

Typically, the collimator 11 is in the form of a plurality of tubes affixed together in a honeycomb like array. One end of each tube is separated from the crystal face 21 by a small distance and the other end is aimed at the focal spot 23 such that radiation is received along rays like rays 12a illustrated in FIG. 1. Of course, the tubes terminate short of the patient aperture 13 to form a truncated fan shaped array. Because the crystal face has significant extent in the direction perpendicular to the scan plane, the collimator is usually configured to simultaneously scan multiple transaxial slices.

In effect, the truncated fan shaped arrangement just described is duplicated in additional planes parallel to the surface of the paper in FIG. 1 so that a plurality of transaxial slices can be scanned in a single rotation of the detector assembly. As described above, the detector with its associated collimator is rotated about the center 19 (FIG. 1) to produce a plurality of projections which are digitized, then fed to a reconstruction computer 16 for producing an image of a cross section of the body and radionuclide concentrations within the cross section for display on a monitor 17.

While the mechanics for taking the projections in the above-described exemplary equipment can and do vary, the common thread binding all the systems is the creation of a projection space and the taking of a plurality of projections at a plurality of angles through the projection space.

Turning now to FIG. 2, it is recalled that the detector 20 is typically a gamma camera having a crystal face 21 and interposed collimators directed through the patient aperture toward the focal point 23 for each transaxial slice, and aimed to form a fan (for each slice). The focal point 23 of the fan and its swath are indicated in FIG. 2. The image space is represented by the pixelized area 22 which can be conceptualized as disposed between the focal spot and the detector/collimator arrangement. In the actual scanning apparatus, the image space is occupied by the body being scanned from which a set of projections is formed. The geometry of FIG. 2 relates the image space to the projections which are collected by the detectors, and after processing, are mapped into the image space to form the reconstructed image.

With respect to the geometry, it is seen that the image space is based on an xy-coordinate system with the origin located at a center of rotation 25 of the system, a fixed distance R from the focal point. The figure illustrates a square pixel array with each pixel of width PWID (measured in units of projection bin width implying that the architecture has been scaled so that distance between adjacent detector bins is unity), having an $(x_i, y_j)$ coordinate with i and j ranging from 1 through NDIM. The single projection illustrated in FIG. 2 is taken at an angle $\zeta$ with respect to the xy-coordinate system.

In a system involving parallel beam geometry, all rays in the projection would be parallel to the center ray 24, simplifying the reconstruction procedure, body edge determination, and method for determining a best-fit ellipse. However, in the fan beam case illustrated in FIG. 2, the rays diverge from the focal point 23 in a fan shaped swath toward the detector. Taking ray 26 as exemplary, it can be identified in coordinates for parallel beam geometry by the normal $\rho$ drawn from the origin to the ray and $\xi$, perpendicular to $\rho$, at the angle $\Psi$ from the xy-coordinate system. Similarly, any arbitrary point in the reconstruction space, such as point 27, can be identified by its polar coordinates $(r,\phi)$.

Figure 3:
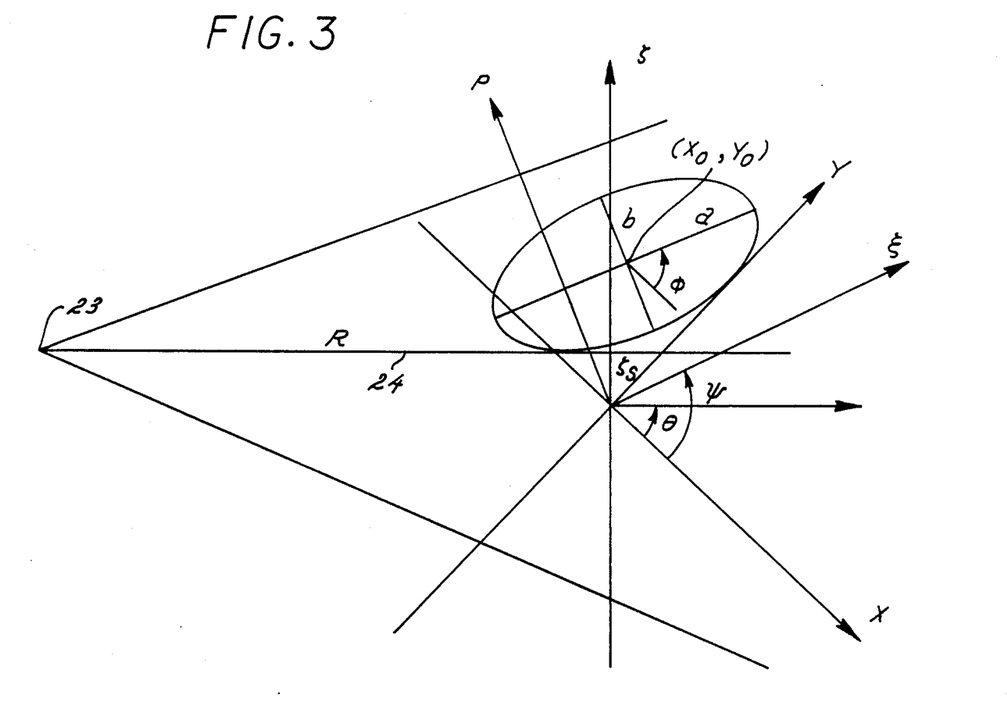
FIG. 3 is an arbitrary ellipse showing the parameters which must be determined from the projection data to define the ellipse, using fan beam geometry, so that it most closely approximates the body boundary contour.

In order to simplify the reconstruction process in a true fan beam system, it is desirable to define yet another coordinate system based on the $\xi$ axis which, as shown in FIG. 3, is normal to central ray 24 and intersects the center of rotation. The $\xi$ axis defines a set of projection bins 1 through KDIM of unit width whose projection information is derived from the detector cells in accordance with the diverging geometry of the fan. Any ray in the fan can be identified by the coordinates $(\xi,\theta)$. Thus, a fan beam projection can be identified by $p(\xi,\theta)$.

Attention will now be directed to the reconstruction process and in particular to estimating the contour of the body to compensate for attenuation in the production of a reconstructed image by defining a set of variable parameters representing an arbitrary elliptical function and determining a final set of parameters which defines an elliptical contour which best fits the scanned body and avoids the necessity for multiple scans. The following explanation considers the continuous analytical solution and supplies the theory and mathematical background underlying the invention. Following the theory, a method and means are described for estimating the elliptical geometric parameters which best estimate the body contour and using that estimate to compensate for attenuation in image reconstruction.

In keeping with the invention, the expected edges of an arbitrary ellipse in fan beam projection space at each of a plurality of angles in terms of variable elliptical parameters are determined. Turning now to FIG. 3, there is illustrated such an arbitrary ellipse in the image space or xy-coordinate system whose variable parameters will ultimately be optimized such that the ellipse most closely approximates the body boundary data. The ellipse in FIG. 3 has an arbitrary and variable center $(x_o, y_o)$ Similarly arbitrary and variable, "a" and "b" have been chosen to represent the semi-major and semi-minor axes, respectively. Additionally, the arbitrary ellipse in FIG. 3 is rotated with respect to the image space by an angle $\phi$. The particular tomographic system illustrated has a center of rotation offset $\xi_s$ from the center line 24 which will be assumed to be zero for purposes of illustration. For a method to compensate for any offset, reference is made to U.S. Pat. No. 4,703,424 and patent application Ser. No. 892,774 filed July 31, 1986. In the above Patent and Application, the instant inventor is a coinventor.

In order to determine the expected edge data, however, the projection function of the arbitrary ellipse must first be found, keeping in mind that a fan beam geometric system is employed. The mathematical expression representing such an arbitrary ellipse is as follows:

$$\frac{[(x - x_o)\cos\phi + (y - y_o)\sin\phi]^2}{a^2} + \frac{[-(x - x_o)\sin\phi + (y - y_o)\cos\phi]^2}{b^2} = 1 \qquad (1)$$

In order to express a projection function for the ellipse as illustrated in FIG. 3 in terms of fan beam geometric coordinates, Equation (1) is first rewritten in terms of parallel beam geometry having coordinates $\rho$ and $\xi$ by using the following coordinate transformation:

$$x = -\rho\sin\Psi + \xi\cos\Psi$$

$$y = \rho\cos\Psi + \xi\sin\Psi \quad (2)$$

Utilizing the coordinate transformation corresponding to parallel beam geometry as given in Equation (2) in the general mathematical formula for the arbitrary ellipse as given in Equation (1) yields the following expression for the arbitrary ellipse expressed in parallel beam geometric coordinates:

$$\frac{[(-\rho\sin\Psi + \xi\cos\Psi - x_o)\cos\phi + (\rho\cos\Psi + \xi\sin\Psi - y_o)\sin\phi]^2}{a^2} + \quad (3)$$

$$\frac{[-(-\rho\sin\Psi + \xi\cos\Psi - x_o)\sin\phi + (\rho\cos\Psi + \xi\sin\Psi - y_o)\cos\phi]^2}{b^2} = 1$$

The first step in determining the expected projection function of the above ellipse requires squaring the bracketed terms and combining like terms. The quadratic formula will then yield an expression for $\xi$ in terms of the projection angle $\Psi$ and the spatial sampling coordinate $\rho$ as given in Equation (4):

$$\xi = \frac{B/2 \pm ab[A - (\rho - C)^2]^{\frac{1}{2}}}{A} \quad (4)$$

where $$A = a^2\sin^2(\Psi - \phi) + b^2\cos^2(\Psi - \phi), \quad (5)$$

$$B = 2a^2\rho\sin(\Psi - \phi)\cos(\Psi - \phi) - \quad (6)$$
$$2b^2\rho\sin(\Psi - \phi)\cos(\Psi - \phi) -$$
$$2a^2\sin(\Psi - \phi)[-x_o\sin\phi + y_o\cos\phi] -$$
$$2b^2\cos(\Psi - \phi)[x_o\cos\phi + y_o\sin\phi]$$

$$C = -x_o\sin\Psi + y_o\cos\Psi. \quad (7)$$

At this point, the projection function for the ellipse in FIG. 3 in terms of the variable parameters of the ellipse is obtained by taking the difference between the two roots for $\xi$ in Equation (4) above, yielding:

$$p(\rho,\Psi) = \begin{cases} \frac{2ab[A - (\rho - C)^2]^{\frac{1}{2}}}{A} & \text{if } A \geq (\rho - C)^2 \\ 0 & \text{otherwise} \end{cases} \quad (8)$$

In keeping with the invention, it is remembered that fan beam geometric systems are employed, and therefore, the expected projection function for the arbitrary ellipse defined by Equation (1) is determined using fan beam geometry. To express the projection function for the ellipse as given in Equation (8) in terms of fan beam coordinates $\zeta$, $\theta$, the following transformation of coordinates is used:

$$\rho = \frac{R(\zeta)}{\sqrt{R^2 + \zeta^2}} \; ; \; \Psi = \theta + \tan^{-1}(\zeta/R) \quad (9)$$

Substituting this transformation of coordinates into the parallel beam projection function yields the following fan beam projection function:

$$p(\zeta,\theta) = \quad (10)$$

$$\begin{cases} \frac{2ab(\zeta^2 + R^2)^{\frac{1}{2}}[A' - (R\zeta - C')^2]^{\frac{1}{2}}}{A'} & \text{if } A' > (R\zeta - C')^2 \\ 0 & \text{otherwise} \end{cases}$$

where $$A' = [R^2(a^2\sin^2(\theta - \phi) + b^2\cos(\theta - \phi)) + \quad (11)$$
$$2R\zeta(a^2 - b^2)\sin(\theta - \phi)\cos(\theta - \phi) +$$
$$\zeta^2(a^2\cos^2(\theta - \phi) + b^2\sin^2(\theta - \phi))]$$

$$C' = [-x_o(R\sin\theta + \zeta\cos\theta) + y_o(R\cos\theta - \zeta\sin\theta)] \quad (12)$$

In order to determine the expected edges of the arbitrary ellipse as in FIG. 3 at each angle in terms of the variable parameters, the projection function as expressed in Equation (10) is set to zero. To determine these edge points, or maximum and minimum coordinates for the projection profile of the ellipse, the expression within the square root in Equation (10) is set to zero. With this requirement, $$A' - (R\zeta - C')^2 = 0 \quad (13)$$

Substituting the expressions for $A'$ and $C'$ as given in Equations (11) and (12), into Equation (13) yields:

$$R^2(a^2s^2 + b^2c^2) + 2R\xi(a^2 - b^2)ac + \xi^2(a^2c^2 + b^2s^2) \\ - [R\xi + x_o(Rs + \xi c) - y_o(Rc - \xi s)]^2 = 0 \quad (14)$$

where $$s = \sin(\theta - \phi); \quad (15)$$

$$c = \cos(\phi - \theta) \quad (16)$$

$$s = \sin(\theta); \quad (17)$$

$$c = \cos(\theta) \quad (18)$$

Squaring the bracketed term and collecting all terms with $\xi^2$, $\xi$, and the remaining constant terms, one obtains the following quadratic equation:

$$D\xi^2 - 2E\xi + F = 0 \quad (19)$$

where $$D = a^2c^2 + b^2s^2 - (R + x_oc + y_os)^2 \quad (20)$$

$$E = R[(x_o^2 - y_o^2)sc + R(x_os - y_oc) + x_oy_o(s^2 - c^2) \\ - (a^2 - b^2)sc] \quad (21)$$

$$F = R^2(a^2s^2 + b^2c^2) - R^2(x_os - y_oc)^2 \quad (22)$$

From the quadratic formula, the two roots of Equation (19) are $$\zeta = \frac{E \pm \sqrt{E^2 - DF}}{D} \tag{23}$$

One root is the minimum coordinate and the other root is the maximum coordinate for the projection profile. These minimum and maximum coordinates are the expected edges of the arbitrary ellipse as defined in Equation (1) in any given projection in fan beam projection space, i.e., the expected edge of the arbitrary ellipse in terms of the variable parameters when projected into fan beam projection space. By averaging the two coordinates one obtains a relationship G such that $$G = (\xi_{max} + \xi_{min})/2 = E/D \tag{24}$$

Substituting for E and D as defined in Equations (20), (21) yields:

$$G = \frac{R[(x_o^2 - y_o^2)sc + R(x_o s - y_o c) +}{a^2 c^2 + b^2 s^2 - (R + x_o c + y_o s)^2} \tag{25}$$

Upon examination, it can be seen that G is both the average of the expected edges of the arbitrary ellipse at each angle in fan beam projection space and is a function of all five of the unknown and variable elliptical parameters, i.e., $x_o, y_o$, a, b and $\phi$.

While the expected edges of the arbitrary ellipse at each angle in terms of the variable parameters, as well as the parameter G relating all of the variable parameters, have been derived in great detail, it will be appreciated that this derivation need not be repeated for each body being scanned. The relationship for G relating all of the variable parameters of the ellipse and the expected projection coordinates for the edges of the ellipse may be stored in the reconstruction computer 16.

In keeping with the invention, a plurality of fan beam projections are taken at a plurality of angles and, from each projection set, apparent body edge data at each view are obtained, i.e., the $\xi_{max}$ and $\xi_{min}$ for each projection angle are determined from the actual recorded projections. One manner of obtaining apparent body edge data is the detection of the ray at which radiation emitted from the body is below a predetermined threshold level.

Figure 4A:
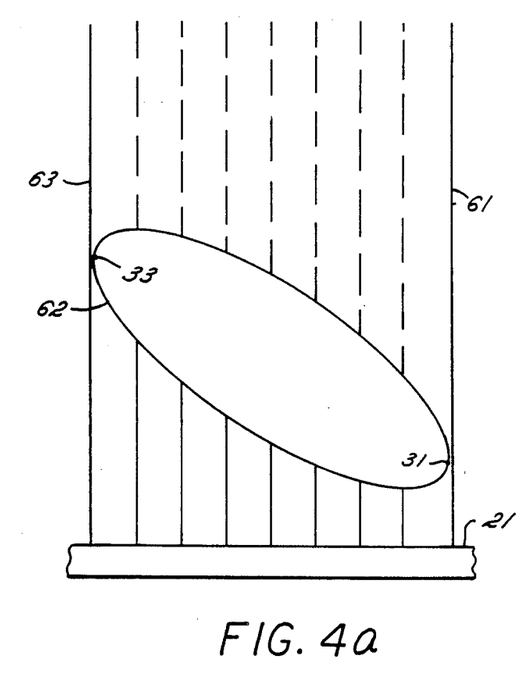
FIGS. 4(a) and 4(b) are diagrams schematically illustrating the rays intersecting elliptical body edges for parallel beam and fan beam systems, respectively.
Figure 4B:
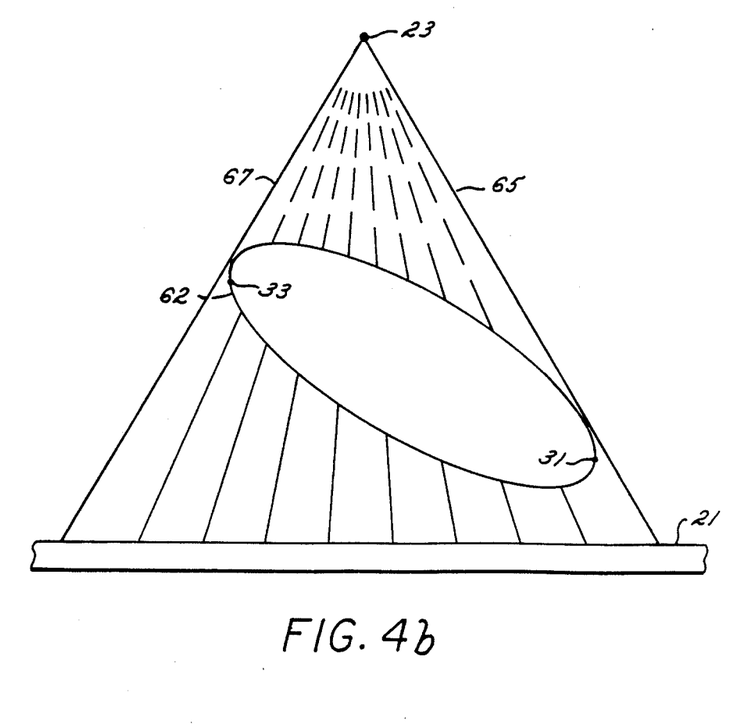

It is emphasized that only apparent body edge data can be obtained. For example, an elliptical body contour 62 is drawn in FIGS. 4(a) and 4(b). The true edges of the body in the illustrated projection view are represented at points 31, 33. These body edge points are the points along the body's axis at which, if projected parallel to the detector 21, the maximum distance occurs. As can be seen, in parallel beam geometry, the rays at which the radiation level falls below a predetermined level, 61, 63 directly relates to the true edges of the body. As can be appreciated by those in the art, a frontal projection and a lateral projection can therefore determine the semi-major and semi-minor axes of an ellipse which will closely approximate the body contour. Additionally, the center coordinates of such an ellipse can be determined with little effort. None of the above simple but accurate processing techniques are applicable for the fan beam case, however. Because of the diverging nature of the fan beam, no substantial information about an ellipse which estimates the body contour can be obtained from a single view, not even from the special views which are normal to the ellipse axes. As illustrated in FIG. 4(b), rays 65, 67 at which radiation falls below a predetermined threshold level, i.e., rays which define the outside of the body, do not give any information about the true body edges 31, 33 in any projection view. Therefore, only apparent body edge data can be obtained in any projection using fan beam geometric systems.

Once the minimum and maximum $\xi$ coordinates, corresponding to the apparent body edge, in each of the fan beam projections are measured, a parameter $G_m$ is determined. $G_m$ is similar to G in that it is the average of the minimum and maximum $\xi$ coordinate at each view, but $G_m$ is determined from the measured apparent body edge at each view, where G is determined from the expected edges of the arbitrary ellipse in fan beam projection space. In order to later estimate the variable parameters, as described in detail below, it is important that G is a function of all five parameters corresponding to the average of the expected edges at each view and that $G_m$ is similar to G but can be determined easily from the actual projection data.

In keeping with another important aspect of the invention, the expected edges of the projected ellipse are fitted to the determined edge coordinates for each projection by iteratively optimizing all of the variable parameters of the arbitrary ellipse to determine a final set of parameters which define an elliptical contour which best fits the scanned body. In contrast to the parallel beam geometric systems where the center of the ellipse $x_o$, $y_o$ can be calculated with linear estimation techniques, the non-linear estimation problem for the fan beam geometry case requires the iterative procedure for all five of the elliptical parameters, thus producing a five-dimension non-linear estimation problem. For example, a first estimate for the variable parameters such as $(x_o, y_o, a, b, \phi) = (0, 0, 3, 5, 0)$ is utilized to determine the parameter G for each view as defined in Equation (25). Parameter G is then compared with $G_m$ taken from the apparent body edge data in fan beam projection space for each of the angles at which the body projections are taken. The sum over all views of the deviation of G from $G_m$ is analyzed and one or more of the five variable parameters $(x_o, y_o, a, b, \phi)$ are adjusted appropriately. The parameter G is redefined based on the adjusted parameters and again compared with $G_m$ for each view. This iterative procedure of modifying the variable parameters and comparing G with $G_m$, for all the views taken, continues until G becomes sufficiently close to $G_m$. The final set of parameters defines an ellipse which is a best fit estimate of the body being scanned.

One such test to determine when G becomes sufficiently close to $G_m$ is to minimize the $x^2$ function relating the apparent body edge data with the arbitrary elliptical parameters as given in Equation (26).

$$\chi^2 = \sum_{m=1}^{N} (G_m - f(x_o, y_o, a, b, \phi))^2 \tag{26}$$

where $$f(x_o, y_o, a, b, \phi) = E/D = G \tag{27}$$

Minimizing the aforesaid chi-square function requires the use of non-linear estimation techniques. An example of the preferred mode of iteratively fitting the expected edge information to the apparent body edge data to estimate the body contour is the Marquardt method described, for example, in the following paper: Gullberg, Tsui, Crawford and Edgerton, "Estimation of Geometrical Parameters For Fan Beam Tomography," *Phys. Med. Biol.* Vol. 32, No. 12, pp. 1581–1594, 1987.

Using the Marquardt method to iteratively solve for a minimum solution to this $\chi^2$ function requires the partial derivatives of the function $f(x_o,y_o,a,b,\phi)$ (set out in Equation (26)) with respect to each of the parameters. These partial derivatives are given as follows:

$$\frac{\partial f}{\partial a} = \frac{D \, \partial E/\partial a - E \, \partial D/\partial a}{D^2} ; \quad \frac{\partial f}{\partial b} = \frac{D \, \partial E/\partial b - E \, \partial D/\partial b}{D^2} \quad (28, 29)$$

$$\frac{\partial f}{\partial \phi} = \frac{D \, \partial E/\partial \phi - E \, \partial D/\partial \phi}{D^2} ; \quad \frac{\partial f}{\partial x_o} = \frac{D \, \partial E/\partial x_o - E \, \partial D/\partial x_o}{D^2} \quad (30, 31)$$

$$\frac{\partial f}{\partial y_o} = \frac{D \, \partial E/\partial y_o - E \, \partial D/\partial y_o}{D^2} ; \quad \frac{\partial D}{\partial a} = 2ac^2 \quad (32, 33)$$

$$\frac{\partial D}{\partial b} = 2bs^2; \quad \frac{\partial D}{\partial \phi} = 2s\,c(a^2 - b^2) \quad (34, 35)$$

$$\frac{\partial D}{\partial x_o} = -2c(R + x_oc + y_os); \quad \frac{\partial D}{\partial y_o} = -2s(R + x_oc + y_os) \quad (36, 37)$$

$$\frac{\partial E}{\partial a} = -2aRs\,c; \quad \frac{\partial E}{\partial b} = 2bRs\,c \quad (38, 39)$$

$$\frac{\partial E}{\partial \phi} = R(a^2 - b^2)(c^2 - s^2); \quad \frac{\partial E}{\partial x_o} = R[2x_osc + Rs + y_o(s^2 - c^2)] \quad (40, 41)$$

$$\frac{\partial E}{\partial y_o} = R[-2y_osc - Rc + x_o(s^2 - c^2)] \quad (42)$$

It will be appreciated that since the expression for G (in terms of the variable elliptical parameters) may be stored in a reconstruction computer as described above, the partial derivatives needed to solve for the function of Equation (26) (as a function of the ellipse variables and other factors relating to the scanner geometry) may be similarly stored and not derived for each application.

By iteratively minimizing the $\chi^2$ function of Equation (26) with the partial derivatives of Equations (28)–(42), the contour of the body is estimated to compensate for attenuation in the production of a reconstructed image.

In the preferred embodiment, a cross sectional image of the body using the plurality of projections is reconstructed using known convolution and back projection techniques designed for use in systems employing fan beam geometry. The cross sectional images, however, are compensated to obtain a truer image by assigning attenuation values to the portion of the image encompassed by the elliptical contour. As discussed in more detail in the Gullberg et al. paper, "Boundary Determination Methods For Attenuation Correction In Single Photon Emission Computed Tomography," any of three types of attenuation correction procedures may be used. In the first type, projection data are first modified to correct for attenuation and then a reconstruction procedure is applied. The second type is a specially designed reconstruction procedure which, itself, corrects for attenuation and is based on mathematically exact solutions and modeled afer the attenuated Radon transform. The third and last type is a post processing correction technique in which the cross sectional image is reconstructed and then each pixel value is increased relative to an average attenuation factor.

Figure 5:
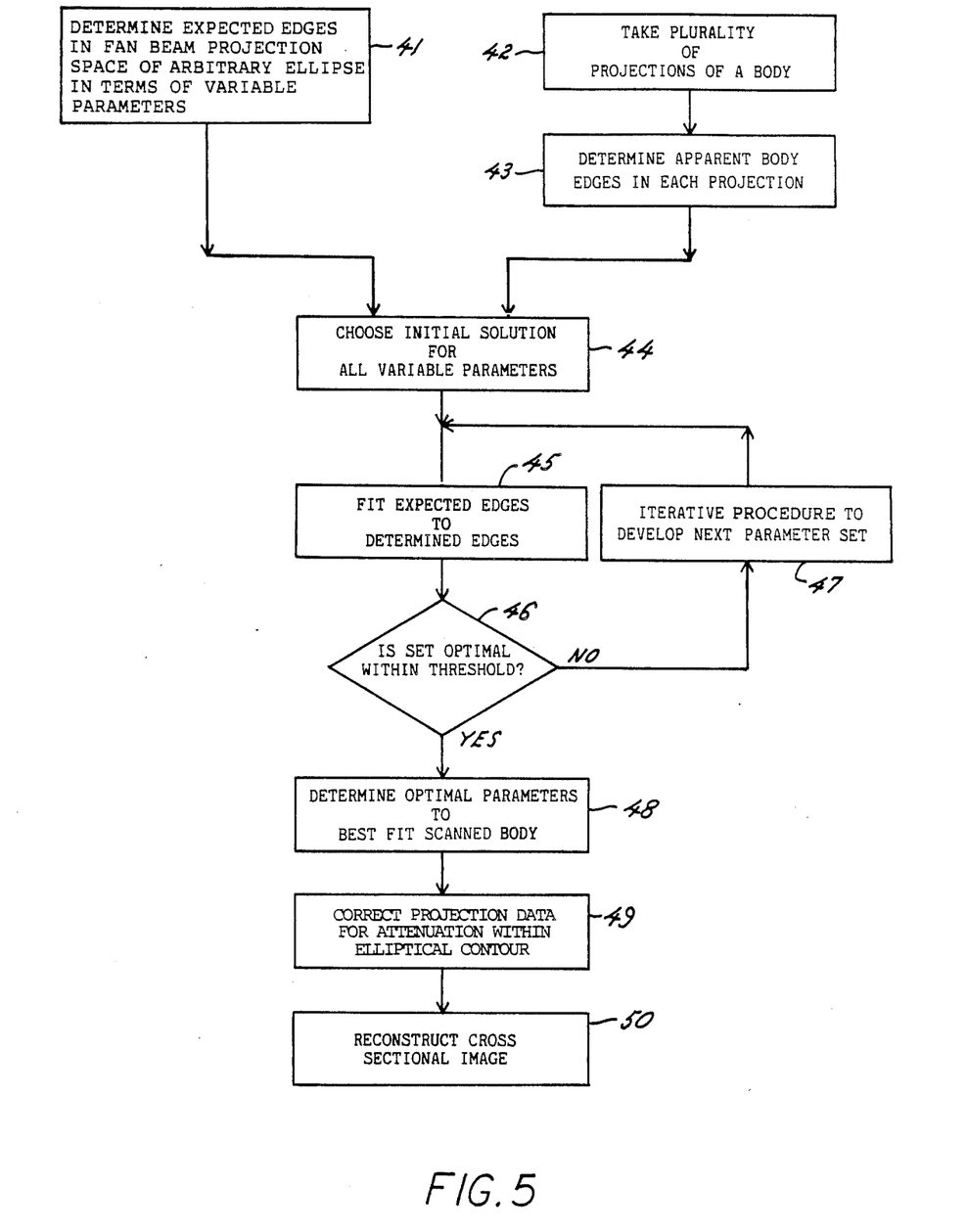
FIG. 5 is a flow chart showing the steps involved in the method of the present invention.

Attention is now directed to FIG. 5 in which a flow chart that presents a method utilizing the underlying mathematical background is described for estimating the body contour to compensate for attenuation in the production of a reconstructed image. A set of variable parameters representing an arbitrary ellipse is defined. The variable parameters include the center of the ellipse, $x_o,y_o$, the semi-minor and semi-major axes of the ellipse, a,b, and the angle of rotation of the ellipse, $\phi$, in the image space. From this set of variable parameters, the arbitrary ellipse is projected into fan beam projection space to determine the expected edges of the arbitrary ellipse at each angle in terms of the variable parameters as shown in Step 41. This step need not be repeated for each reconstructed image, but the relationship defining expected edge coordinates in terms of the ellipse variables may be stored in a reconstruction computer as described above.

Additionally, at Step 42, a plurality of fan beam projections of a body being scanned at a plurality of angles is taken and, at Step 43, fan beam coordinates of the apparent body edge ($\xi_{min},\xi_{max}$) in each projection angle are determined. The body edge in each projection in fan beam emission computed tomography systems is often determined by detecting the point at which radiation levels fall below a predetermined level. Information from Steps 41 and 43 is then used at Steps 44–47 where the expected edges of the projected ellipse are fitted to the determined edge coordinates for each projection by iteratively optimizing all of the variable parameters of the arbitrary ellipse to determine a final set of parameters which defines an elliptical contour which best fits the scanned body.

In greater detail, Step 44 is shown wherein an initial solution set containing values for all five elliptical parameters is selected, such as $(x_o,y_o,a,b,\phi)=(0,0,3,5,0)$. This solution set is then fitted to the apparent body edge data in each projection (Step 46), i.e., G and $G_m$ are determined, compared and tested, to see if it is the optimal solution to best estimate the body contour. Since the solution requires a non-linear iterative estimation technique such as the Marquardt method, a threshold level for optimization is incorporated at Step 46. The optimizing procedure will continue to iteratively vary the elliptical parameters (Step 47) until an optimal set of elliptical parameters is obtained (Step 48).

Thereafter, in the illustrated method, a cross sectional image of the body using the same projections as were used to determine the body contour is reconstructed using convolution and back projection techniques designed for fan beam systems. More particularly, the projection data taken in Step 42, above, are corrected for attenuation (Step 49) within the elliptical contour defined by the optimal set of parameters as described above in Step 48. The subsequently reconstructed cross-sectional image is then a truer and more accurate cross sectional image of the scanned body with respect to source intensities. This procedure, as well as the other attenuation correction procedures for image reconstruction discussed above, are presented in more detail in the above-referenced Gullberg et al. paper entitled "Boundry Determination Methods For Attenuation Correction In Single Photon Emission Computed Tomography."

The method of the invention, described in detail above, can be practiced in concert with the reconstruction computer 16 (FIG. 1) which is an element of the CT system. More particularly, the computer 16 can be programmed to carry out the steps of the method, and when properly programmed by those skilled in the art based on the foregoing disclosure, comprises an apparatus for estimating the contour of a scanned body to compensate for attenuation in fan beam computed tomographic reconstructions.

In summary, it can be seen that in emission fan beam computed tomographic systems that have a detector system for taking a plurality of projections of a body at a plurality of angles, a means and method has been provided for estimating the body contour. The presented method allows for the determination of elliptical parameters which define an ellipse that closely estimates the body boundary contour in systems that use fan beam geometry using fan beam projection data and does not require the use of multiple scan techniques.

I claim:

1. In fan beam computed tomographic systems having a detector system for taking a plurality of projections of a scanned body at a plurality of angles, a method of estimating the contour of the body comprising the steps of:
    determining expected edges of an arbitrary ellipse in fan beam projection space at each angle in terms of variable elliptical parameters;
    taking a plurality of fan beam projections of a body being scanned at a plurality of angles;
    determining from each fan beam projection the fan beam coordinates of the apparent body edge in each of the projections;
    fitting the expected edges of the projected ellipse to the determined edge coordinates for each fan beam projection by iteratively optimizing a function relating all of the variable parameters of the arbitrary ellipse to determine a final set of parameters which defines an elliptical contour which best fits the scanned body, and
    processing the fan beam projections in conjunction with the defined elliptical contour to produce a reconstructed cross sectional image of the scanned body within the defined elliptical contour.

2. The method of claim 1 wherein said fan beam computed tomographic system is an emission fan beam computed tomographic system, and the step of processing further comprises the step of reconstructing a cross sectional image of the body using the plurality of fan beam projections by assigning attenuation values to the portion of the image encompassed by the elliptical contour.

3. The method of claim 2 wherein said optimizing is performed with the Marquardt method.

4. The method of claim 2 wherein said parameters include the center coordinates, semi-minor and semi-major axes,, and angle of rotation of the ellipse with respect to an image space.

5. The method of claim 2 wherein the computed tomographic system further includes a gamma camera and a converging collimator disposed for rotation about the given center of rotation to take the projections.

6. The method of claim 2 wherein the expected edges define the fan beam projection coordinates $(\xi,\theta)$ of the rays passing through the edges of arbitrary ellipse in terms of the variable elliptical parameters defining said arbitrary ellipse, and the apparent body edges are measured from the actual fan beam projection coordinates of the body boundary in any given view.

7. The method of claim 6 wherein the apparent body edges are determined by rays having an intensity below a predetermined threshold.

8. The method of claim 7 wherein the apparent body edges are the $\xi_{max}$ and $\xi_{min}$ measured in each projection angle, and the expected edges are the expected $\xi_{max}$ and $\xi_{min}$ in each angle in terms of the variable elliptical parameters.

9. The method of claim 8 wherein the variable elliptical parameters are the center coordinates $x_0, y_0$; the semi-major and semi-minor axes a,b; and the angle of rotation of the ellipse with respect to image space $\phi$.

10. In fan beam computed tomographic systems having a detector system for taking a plurality of projections of a scanned body at a plurality of angles, an apparatus for estimating the contour of the body comprising, in combination:
    means for defining the expected edges, in fan beam projection space, of an arbitrary ellipse at each of a plurality of angles in terms of variable elliptical parameters;
    means for taking a plurality of fan beam projections having sufficient information to reconstruct a cross sectional image of the scanned body;
    means operative on each fan beam projection for determining the fan beam coordinates of the apparent body edge in each of the plurality of fan beam projections;
    means for fitting the expected edges of the projected ellipse to the determined edge coordinates for each fan beam projection by iteratively optimizing a function relating all of the variable parameters of the arbitrary ellipse to determine a final set of parameters which defines an elliptical contour which best fits the scanned body, and
    means for processing the fan beam projections in conjunction with the defined elliptical contour to produce a reconstructed cross sectional image of the scanned body within the defined elliptical contour.

11. An apparatus as defined in claim 10 wherein said fan beam computed tomographic system is an emission fan beam computed tomographic system, and the means for processing further comprises means for reconstructing a cross sectional image of the body using the plurality of fan beam projections by assigning attenuation values to the portion of the image encompassed by the elliptical contour.

12. An apparatus as defined in claim 11 wherein said optimizing is performed with the Marquardt method.

13. An apparatus as defined in claim 11 wherein said parameters include the center coordinates, semi-minor and semi-major axes, and angle of rotation of the ellipse with respect to an image space.

14. An apparatus as defined in claim 11 wherein the expected edges define the fan beam projection coordinates ($\xi,\phi$) of the rays passing through the arbitrary ellipse edges in terms of the elliptical contour defined by its variable elliptical parameters, and the apparent body edges are measured from the fan beam projection coordinates of the body boundary in any given view.

15. An apparatus as defined in claim 11 wherein the expected edges define the fan beam projection coordinates ($\xi,\phi$) of the rays passing through the edges of arbitrary ellipse in terms of the variable elliptical parameters defining said arbitrary ellipse, and the apparent body edges are measured from the actual fan beam projection coordinates of the body boundary in any given view.

16. The apparatus of claim 15 wherein the apparent body edges are determined by rays having an intensity below a predetermined threshold.

17. The apparatus of claim 16 wherein the apparent body edges are the $\xi_{max}$ and $\xi_{min}$ measured in each projection angle, and the expected edges are the expected $\xi_{max}$ and $\xi_{min}$ in each angle in terms of the variable elliptical parameters.

18. The apparatus of claim 17 wherein the variable elliptical parameters are the center coordinates $x_o,y_o$; the semi-major and semi-minor axes a,b; and the angle of rotation of the ellipse with respect to image space $\phi$.

* * * * *